United States Patent
Meister et al.

(10) Patent No.: US 8,489,194 B2
(45) Date of Patent: Jul. 16, 2013

(54) ENHANCING FINE TIME STRUCTURE TRANSMISSION FOR HEARING IMPLANT SYSTEM

(75) Inventors: Dirk Meister, Axams (AT); Peter Schleich, Telfs (AT); Peter Nopp, Birgitz (AT)

(73) Assignee: Med-El Elektromedizinische Geraete GmbH, Innbruck (AT)

( * ) Notice: Subject to any disclaimer, the term of this patent is extended or adjusted under 35 U.S.C. 154(b) by 0 days.

(21) Appl. No.: 13/370,469

(22) Filed: Feb. 10, 2012

(65) Prior Publication Data

US 2012/0209351 A1 Aug. 16, 2012

Related U.S. Application Data (60) Provisional application No. 61/442,431, filed on Feb. 14, 2011.

(51) Int. Cl.
*A61N 1/04* (2006.01)
*H04R 25/00* (2006.01)

(52) U.S. Cl.
USPC ............... 607/55; 607/57; 607/137; 381/320

(58) Field of Classification Search
USPC . 381/312, 316, 317, 318, 320; 600/25; 607/1, 607/2, 55–57, 136, 137
See application file for complete search history.

(56) References Cited

U.S. PATENT DOCUMENTS

| | | | |
|---|---|---|---|
| 4,536,844 A | 8/1985 | Lyon | 607/56 |
| 5,271,397 A | 12/1993 | Seligman et al. | 607/137 |
| 5,749,912 A | 5/1998 | Zhang et al. | 607/57 |
| 6,594,525 B1 | 7/2003 | Zierhofer | 607/57 |
| 7,139,403 B2 | 11/2006 | Richardson et al. | 381/107 |
| 7,225,027 B2 | 5/2007 | Zeng et al. | 607/57 |
| 7,231,257 B2 | 6/2007 | McDermott et al. | 607/57 |
| 7,283,876 B2 | 10/2007 | Zierhofer | 607/57 |
| 7,317,945 B2 | 1/2008 | Litvak et al. | 607/57 |

(Continued)

FOREIGN PATENT DOCUMENTS

| | | |
|---|---|---|
| WO | WO 2009/012151 | 1/2009 |
| WO | WO 2009/126680 | 10/2009 |

OTHER PUBLICATIONS

"9th International Conference on Cochlear Implants and Related Sciences," *Wiener Medizinische Wochenschrift*, Springer-Verlag, vol. 156, No. 119, pp. 1-192, Jun. 2006.

(Continued)

*Primary Examiner* — Brian T Gedeon
(74) *Attorney, Agent, or Firm* — Sunstein Kann Murphy & Timbers LLP (57) ABSTRACT

A system and method of signal processing for a hearing implant. The hearing implant includes at least one electrode, each electrode associated with a channel specific sampling sequence. An acoustic audio signal is processed to generate for each electrode a band pass signal representing an associated band of audio frequency. For each electrode, a sequence signal is determined as a function of the electrode's associated band pass signal and channel specific sampling sequence. An envelope of each band pass signal is determined. The envelope of each band pass signal is filtered to reduce modulations resulting from unresolved harmonics, creating for each electrode an associated filtered envelope signal. Each electrode's sequence signal is weighted based, at least in part, on the electrode's associated filtered envelope signal.

22 Claims, 6 Drawing Sheets

U.S. PATENT DOCUMENTS

| | | | | |
|---|---|---|---|---|
| 7,542,806 | B1 | 6/2009 | Voelkel | 607/56 |
| 8,285,385 | B2 * | 10/2012 | Schleich | 607/57 |
| 8,374,699 | B2 * | 2/2013 | Meister et al. | 607/57 |
| 2005/0203590 | A1 | 9/2005 | Zierhofer | 607/57 |
| 2005/0222644 | A1 | 10/2005 | Killian et al. | 607/57 |
| 2006/0052841 | A1 | 3/2006 | Daly et al. | 607/57 |
| 2006/0080087 | A1 | 4/2006 | Vandali et al. | 704/207 |
| 2006/0227986 | A1 | 10/2006 | Swanson et al. | 381/312 |
| 2007/0156202 | A1 | 7/2007 | Zierhofer | 607/57 |
| 2008/0215332 | A1 | 9/2008 | Zeng et al. | 704/271 |
| 2009/0018614 | A1 | 1/2009 | Zierhofer | 607/56 |
| 2009/0254150 | A1 | 10/2009 | Zierhofer | 607/57 |
| 2010/0070000 | A1 | 3/2010 | Litvak et al. | 607/57 |
| 2010/0198300 | A1 | 8/2010 | Smith | 607/57 |
| 2010/0204755 | A1 | 8/2010 | Meister | 607/57 |

OTHER PUBLICATIONS

Loizou, "Signal-Processing Techniques for Cochlear Implants," *IEEE Engineering in Medicine and Biology*, vol. 18, No. 3, pp. 34-46, May 1999.

Luo et al., Poster Session—"Enhancing Chinese Tone Recognition by Manipulating Amplitude Contour: Implications for Cochlear Implants", 2003 Conference on Implantable Auditory Prostheses, 23 pages, Aug. 2003.

Wilson, et al. "Better Speech Recognition with Cochlear Implants," *Nature*, vol. 352, pp. 236-238, Jul. 1991.

International Searching Authority, International Search Report—International Application No. PCT/US2008/069799—dated Nov. 3, 2008, together with the Written Opinion of the International Searching Authority, 14 pages.

European Patent Office, Extended European Search Report—Application No. 09730486.9-2305/2263388 dated Dec. 29, 2011, 9 pages.

International Searching Authority, International Search Report—International Application No. PCT/US12/24600 dated Jun. 22, 2012, together with the Written Opinion of the International Searching Authority, 10 pages.

Luo et al., "Frequency Modulation Detection with Simultaneous Amplitude Modulation by Cochlear Implant Users", *J. Acoust. Soc. Am*, vol. 122 (2), pp. 1046-1057, Aug. 2007.

Drullman et al., "Effect of Reducing Slow Temporal Modulations on Speech Reception", *J. Acoust. Soc. Am*, vol. 95 (5), pp. 2670-2680, May 1994.

Middlebrooks, "Auditory Cortex Phase Locking to Amplitude-Modulated Cochlear Implant Pulse Trains", *J. Neruophisiol*, vol. 100, pp. 76-91, Mar. 2008.

Moore et al., "Detection of Frequency Modulation by Hearing-Impaired Listeners: Effects of Carrier Frequency, Modulation Rate, and Added Amplitude Modulation", *J. Acoust. Soc. Am.*, vol. 111 (1), pp. 327-335, Jan. 2002.

Shannon et al., "Speech Recognition with Primarily Temporal Cues", *Science*, vol. 270, No. 5234, pp. 303-304, Oct. 1995.

Steeneken et al., "A Physical Method for Measuring Speech-Transmission Quality", *J. Acoust. Soc. Am.*, vol. 67 (1), pp. 318-326, Jan. 1980.

Zeng et al., "Auditory Perception with Slowly-Varying Amplitude and Frequency Modulations", In: Presnitzer et al. *Auditory Signal Processing: Physiology, Psychoacoustics, and Models*, Springer Verlag, New York, pp. 237-243, 2004.

* cited by examiner

ENHANCING FINE TIME STRUCTURE TRANSMISSION FOR HEARING IMPLANT SYSTEM

CROSS-REFERENCE TO RELATED APPLICATIONS

The present application claims priority from U.S. provisional application Ser. No. 61/442,431, entitled "Enhancing Fine Time Structure Transmission for Hearing Implant System," filed Feb. 14, 2011, which is hereby incorporated herein by reference in its entirety.

TECHNICAL FIELD

The present invention relates to acoustic signal processing for a hearing implant, and more particularly, to a speech coding methodology and system for a cochlear implant.

BACKGROUND ART

Figure 1:
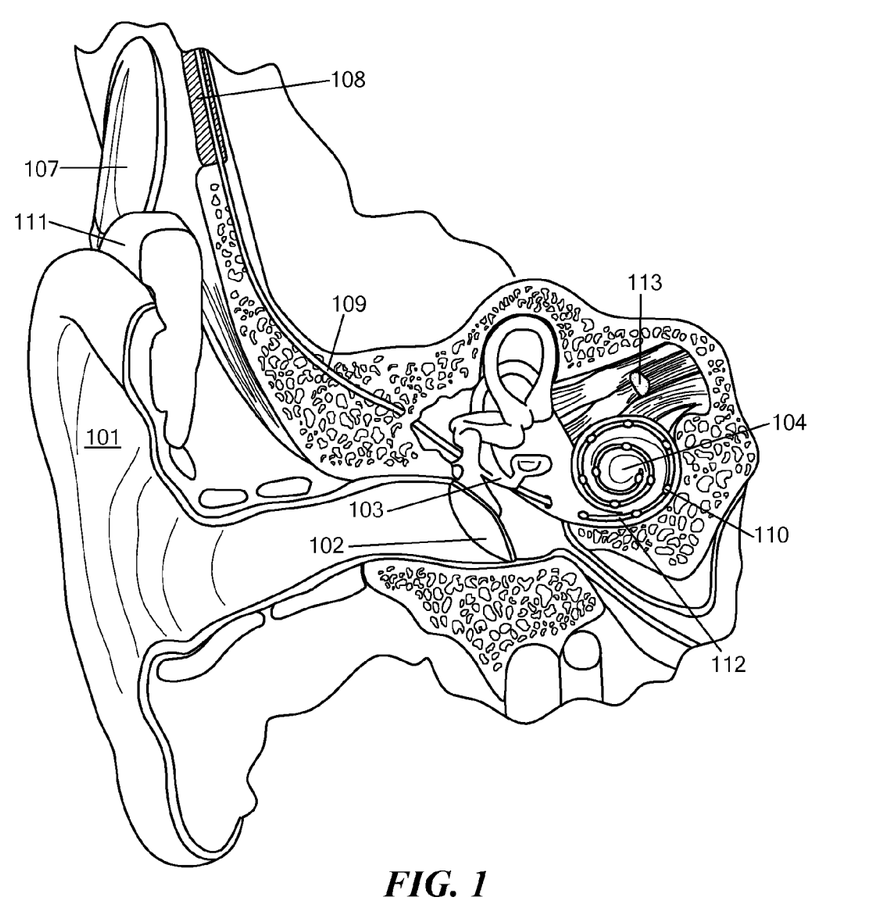
FIG. 1 shows anatomical structures of a human ear and some components of a typical cochlear implant system.

A normal ear transmits sounds as shown in FIG. 1 through the outer ear 101 to the tympanic membrane (eardrum) 102, which moves the bones of the middle ear 103, which in turn vibrate the oval window and round window openings of the cochlea 104. The cochlea 104 is a long narrow duct wound spirally about its axis for approximately two and a half turns. The cochlea 104 includes an upper channel known as the scala vestibuli and a lower channel known as the scala tympani, which are connected by the cochlear duct. The scala tympani forms an upright spiraling cone with a center called the modiolar where the spiral ganglion cells of the acoustic nerve 113 reside. In response to received sounds transmitted by the middle ear 103, the fluid filled cochlea 104 functions as a transducer to generate electric pulses that are transmitted to the cochlear nerve 113, and ultimately to the brain.

Hearing is impaired when there are problems in the ability to transduce external sounds into meaningful action potentials along the neural substrate of the cochlea 104. In some cases, hearing impairment can be addressed by an auditory prosthesis system such as a cochlear implant that electrically stimulates auditory nerve tissue with small currents delivered by multiple electrode contacts distributed along an implant electrode. FIG. 1 shows some components of a typical cochlear implant system where an external microphone provides an audio signal input to an external signal processing stage 111 which implements one of various known signal processing schemes. The processed signal is converted by the external signal processing stage 111 into a digital data format, such as a sequence of data frames, for transmission into a receiver processor in an implant housing 108. Besides extracting the audio information, the receiver processor in the implant housing 108 may perform additional signal processing, and produces a stimulation pattern (based on the extracted audio information) that is sent through an electrode lead 109 to an implanted electrode array 112 which penetrates into the cochlea 104 through a surgical opening called a cochleostomy. Typically, this electrode array 112 includes multiple electrode contacts 110 on its surface that deliver the stimulation signals to adjacent neural tissue of the cochlea 104 which the brain of the patient interprets as sound. The individual electrode contacts 110 may be activated sequentially, or simultaneously in one or more contact groups.

Perception of music and prosodic speech cues are still challenging tasks for cochlear implant users. An audio signal, such as speech or music can be decomposed into the signal amplitude and the fine time structure. The envelope of the signal is fluctuating in amplitude over time and may therefore be considered as the amplitude-modulation of the signal. The fine time structure is fluctuating in frequency over time and may be considered equivalent to the frequency-modulated (FM) carrier wave of the signal.

Speech coding strategies for cochlear implants encode acoustic signals into electrical pulses that stimulate the acoustic nerve. Acoustic frequency can be encoded into a varying pulse rate, because different pulse rates are perceived as different in pitch by cochlear implant users.

One common speech coding strategy is the is the so called "continuous-interleaved-sampling strategy" (CIS), as described by Wilson B. S., Finley C. C., Lawson D. T., Wolford R. D., Eddington D. K., Rabinowitz W. M., "Better speech recognition with cochlear implants," Nature, vol. 352, 236-238 (July 1991), which is hereby incorporated herein by reference. The CIS speech coding strategy samples the signal envelope amplitude modulation (AM) at predetermined time intervals, providing a remarkable level of speech understanding merely by coding the AM of the speech signal. This can be explained, in part, by the fact that auditory neurons phase lock to amplitude modulated (AM) electrical pulse trains (see, for example, Middlebrooks, J. C., "Auditory Cortex Phase Locking to Amplitude-modulated Cochlear Implant Pulse Trains," J Neurophysiol, 100(1), p. 76-912008, 2008 July, which is hereby incorporated herein by reference). However, both cues, FM and AM, are important for normal hearing subjects (see, for example, Zeng F., Nie K., Stickney G., Kong Y., "Auditory Perception with Slowly-varying Amplitude and Frequency Modulations," In: D. Pressnitzer, A. de Cheveign'e, S. McAdams, and L. Collet, "Auditory Signal Processing: Physiology, Psychoacoustics, and Models, Springer Verlag, New York, pp. 237-243, 2004, which is hereby incorporated herein by reference). The perception of frequency modulation cues can be disturbed by a simultaneous AM (see, for example: Moore B. C., Skrodzka E., "Detection of Frequency Modulation by Hearing-impaired Listeners: Effects of Carrier Frequency, Modulation Rate, and Added Amplitude Modulation" J Acoust Soc Am, 111(1 Pt 1), p. 327-335, 2002 January, which is hereby incorporated herein by reference). FM Detection Thresholds (FMDTs) significantly worsen in the presence of simultaneous AM in cochlear implant users (see Luo X., Fu Q., "Frequency Modulation Detection with Simultaneous Amplitude Modulation by Cochlear Implant Users," J Acoust Soc Am, 122(2), p. 1046-1054, 2007, which is hereby incorporated herein by reference), and the fine time structure cues may thus be masked from the cochlear implant user by simultaneous temporal envelope modulation.

Current speech coding strategies code mainly slow varying signal envelope information and do not transmit the fine time structure of a signal. As these strategies code mainly envelope information, they generally do not suffer from the domination of AM over FM.

In contrast, when strategies do code fine time structure, amplitude modulations resulting from unresolved harmonics can interfere with, and partially mask the fine time structure information.

A clinically available coding strategy that transmits fine structure cues is Fine Structure Processing (FSP). In FSP, the fine time structure of low frequency channels is transmitted through Channel Specific Sampling Sequences (CSSS) that start at negative to positive zero crossings of the respective band pass filter output (see U.S. Pat. No. 6,594,525, Zierhofer 2003, which is hereby incorporate by reference herein). The basic idea is to apply a stimulation pattern, where a particular relationship to the center frequencies of the filter channels is preserved, i.e., the center frequencies are represented in the temporal waveforms of the stimulation patterns, and are not fully removed, as in CIS. Each stimulation channel is associated with a particular CSSS, which is a sequence of ultra-high-rate biphasic pulses (typically 5-10 kpps). Each CSSS has a distinct length (number of pulses) and distinct amplitude distribution. The length of a CSSS may be derived, for example, from the center frequency of the associated band pass filter. A CSSS associated with a lower filter channel is longer than a CSSS associated with a higher filter channel. For example, it may be one half of the period of the center frequency. The amplitude distribution may be adjusted to patient specific requirements.

Figure 2A:
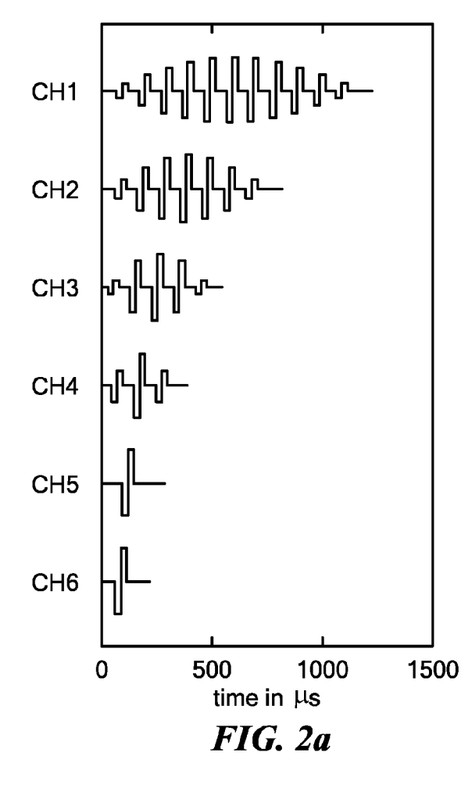
FIG. 2 shows channel specific sampling sequences (CSSS) for two 6-channel systems utilizing biphasic pulses at 10 kpp/s and phase duration of 25 μs
  a. derived from a sinusoid within [0–π]
  b. derived from a sinusoid within [0–π/2], amplitudes monotonically increasing.
Figure 2B:
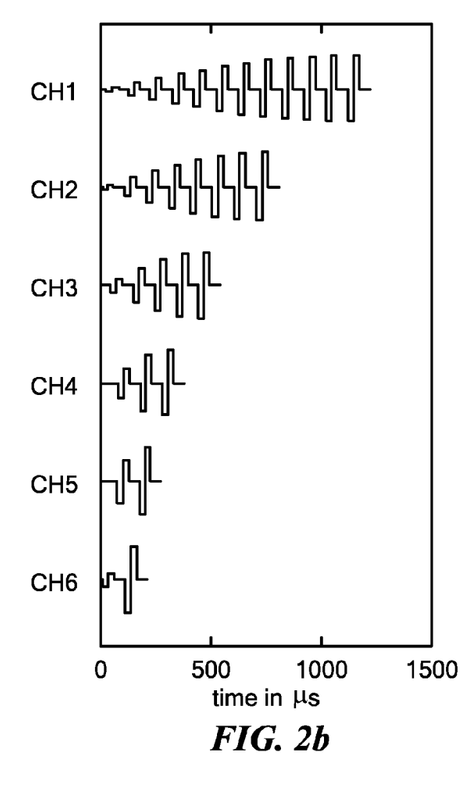

For illustration, two examples for a 6-channel system are shown. In FIG. 2(a), the CSSS's are derived by sampling one half of a period of a sinusoid, whose frequency is equal to the center frequency of the band pass filter (center frequencies at 440 Hz, 696 Hz, 1103 Hz, 1745 Hz, 2762 Hz, and 4372 Hz). Sampling is achieved by means of biphasic pulses at a rate of 10 kpps and a phase duration of 25 µs. For channels #5 and #6, one half of a period of the center frequencies is too short to give space for more than one stimulation pulse, i.e., the "sequences" consist of only one pulse, respectively. Other amplitude distributions may be utilized. For example, in FIG. 2(b), the sequences are derived by sampling one quarter of a sinusoid with a frequency, which is half the center frequency of the band pass filters. These CSSS's have about the same durations as the CSSS's in FIG. 2(a), respectively, but the amplitude distribution is monotonically increasing. Such monotonic distributions might be advantageous, because each pulse of the sequence can theoretically stimulate neurons at sites which cannot be reached by its predecessors.

Figure 3:
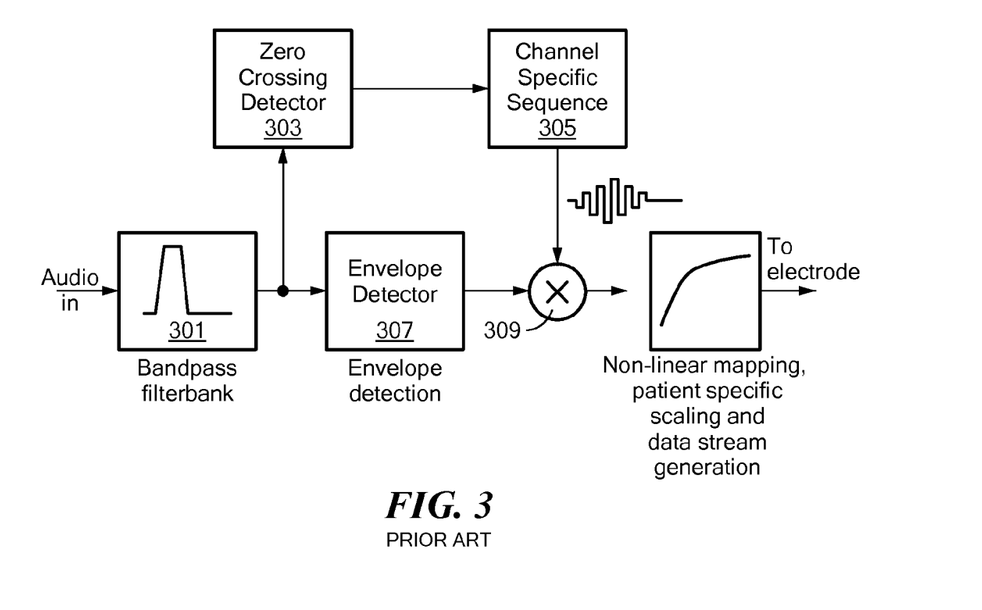
FIG. 3 shows a prior art fine structure processing (FSP) scheme.

FIG. 3 (prior art) illustrates an exemplary signal processing scheme of the FSP strategy. The audio signal is first split up into spectral bands by means of a filter bank of band pass filters 301. Each of these spectral bands is then further processed by a zero crossing detector 303 that detects the negative to positive zeros crossings of each spectral band. The CSSS 305 are inserted at the start of the negative to positive zero crossings of their respective band pass filter output. An envelope detector 307 provides the envelopes of band pass time signals, which include unresolved harmonics and are modulated with the difference tones of the harmonics, mainly the fundamental frequency F0. When the CSSS stimulation pulses are weighted 309 with these envelopes, the resulting pulses are undesirably amplitude modulated mainly with F0. This also applies to the frequency bands that are designed to transmit fine time structure, in addition to amplitude cues.

SUMMARY OF THE EMBODIMENTS

In accordance with a first embodiment of the invention there is provided a method of signal processing for a hearing implant. The hearing implant includes at least one electrode, each electrode associated with a channel specific sampling sequence. The method includes processing an acoustic audio signal to generate for each electrode a band pass signal representing an associated band of audio frequency. For each electrode, a sequence signal is determined as a function of the electrode's associated band pass signal and channel specific sampling sequence. An envelope of each band pass signal is determined. The envelope of each band pass signal is filtered to reduce modulations resulting from unresolved harmonics, creating for each electrode an associated filtered envelope signal. Each electrode's sequence signal is weighted based, at least in part, on the electrode's associated filtered envelope signal.

In accordance with related embodiments of the invention, filtering the envelope of each band pass signal may include low pass filtering. Low pass filtering may include using a cut-off frequency that is lower than the fundamental frequency of the acoustic audio signal. For example, the low pass filtering may include using a cut-off frequency $f_c$ of 15 Hz$\leq f_c \leq$90 Hz. Filtering the envelope of each band pass signal may include removing the fundamental frequency associated with the band pass signal. Filtering the envelope of each band pass filter may result in a filtered envelope signal with only one harmonic. Filtering the envelope may include using a psychoacoustic masking model, or a high resolution filter bank.

In accordance with further related embodiments of the invention, determining for each electrode a sequence signal as a function of the electrode's associated band pass signal and channel specific sampling sequence may include rectifying the electrode's associated band pass signal to create a half-wave rectified signal. Each half-wave is replaced with the associated electrode's channel specific sampling sequence.

In accordance with still further related embodiments of the invention, determining for each electrode a sequence signal as a function of the electrode's associated band pass signal and channel specific sampling sequence may include determining negative to positive zero crossings of the electrode's associated band pass signal. The electrode's associated channel specific sampling sequence is inserted at the negative to positive zero crossings.

In accordance with yet further related embodiments of the invention, the method may include stimulating the at least one electrode based, at least in part, on their associated weighted sequence signal. The hearing implant may be a cochlear implant which stimulates the acoustic nerve.

In accordance with another embodiment of the invention, a hearing system includes at least one electrode. Each electrode is associated with a channel specific sampling sequence. A signal processor is configured to process an acoustic audio signal to generate for each electrode a band pass signal representing an associated band of audio frequency. Furthermore the signal processor is configured to determine for each electrode a sequence signal as a function of the electrode's associated band pass signal and channel specific sampling sequence. An envelope of each band pass signal is determined by the signal processor, with the envelope of each band pass signal filtered to reduce modulations resulting from unresolved harmonics, creating for each electrode an associated filtered envelope signal. Each electrode's sequence signal is weighted based, at least in part, on the electrode's associated filtered envelope signal.

In accordance with related embodiments of the invention, the signal processor may include a low pass filter for filtering the envelope of each band pass signal. The low pass filter may include a cut-off frequency that is lower than the fundamental frequency of the acoustic audio signal. The low pass filter may include, for example, a cut-off frequency $f_c$ of 15 Hz$\leq f_c \leq$90 Hz. The low pass filter may remove the fundamental frequency associated with the band pass signal. The signal processor may include a psychoacoustic masking model for filtering the envelope of each band pass signal to create a filtered envelope signal with only one harmonic. The signal processor may include a high resolution filter bank for filtering the envelope of each band pass signal to create a filtered envelope signal with only one harmonic.

In accordance with further related embodiments of the invention, the signal processor may include a rectifier for rectifying the electrode's associated band pass signal to create a half-wave rectified signal. The signal processor may be configured to replace each half-wave with the associated electrode's channel specific sampling sequence in determining the sequence signal.

In accordance with still further related embodiments of the invention, the signal processor may include a zero crossing detector for determining negative to positive zero crossings of the electrode's associated band pass signal. The signal processor may be configured to insert at the negative to positive zero crossings the electrode's associated channel specific sampling sequence in determining the sequence signal.

In accordance with yet further related embodiments of the invention, the hearing system may include a stimulator for stimulating the at least one electrodes based, at least in part, on their associated weighted sequence signal. The hearing system may be a cochlear prosthesis system, with the stimulator capable of being implanted so as to stimulate the acoustic nerve.

In accordance with another embodiment of the invention, a computer program product for processing signals associated with a hearing implant is provided. The hearing implant includes at least one electrode, each electrode associated with a channel specific sampling sequence. The computer program product includes a computer usable medium having computer readable program code thereon. The computer readable program code includes program code for generating a band pass signal for each electrode representing an associated band of audio frequency based at least in part, on an acoustic audio signal. The computer readable program code further includes program code for; determining for each electrode a sequence signal as a function of the electrode's associated band pass signal and channel specific sampling sequence; determining an envelope of each band pass signal; and for filtering the envelope of each band pass signal to reduce modulations resulting from unresolved harmonics, creating for each electrode an associated filtered envelope signal. The computer readable program code still further includes program code weighting each electrode's sequence signal based, at least in part, on the electrode's associated filtered envelope signal.

BRIEF DESCRIPTION OF THE DRAWINGS

The foregoing features of embodiments will be more readily understood by reference to the following detailed description, taken with reference to the accompanying drawings, in which.

DETAILED DESCRIPTION OF SPECIFIC EMBODIMENTS

Illustrative embodiments of the invention include systems and methods of enhancing fine time structure perception of hearing prosthesis users, such as a cochlear implant users. Generally, the system and method includes reducing modulations in the band pass signal envelope resulting from unresolved harmonics, particularly in those channels designed to transmit fine time structure. Details are discussed below.

Figure 4:
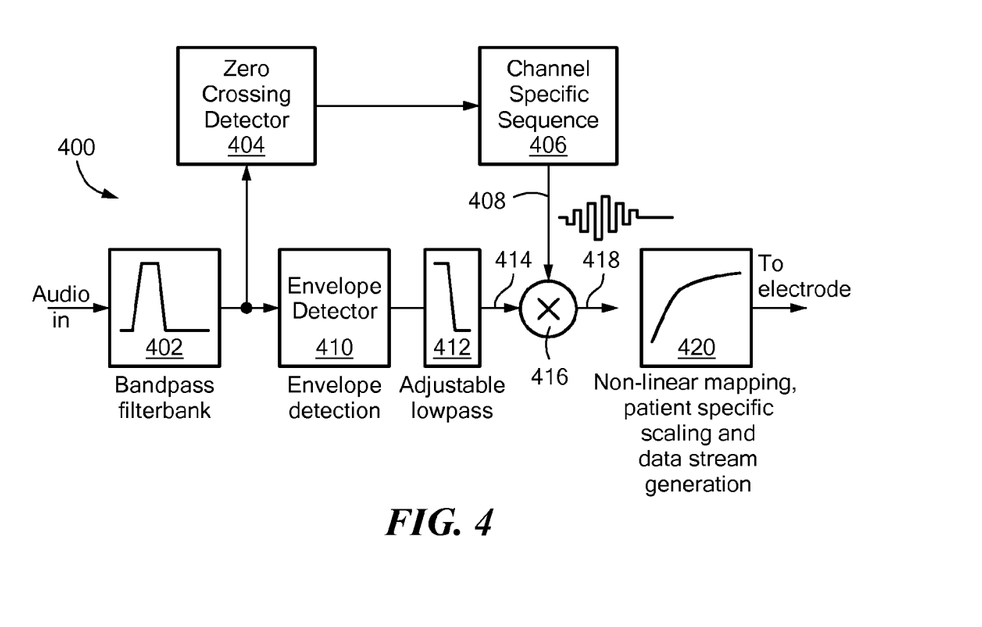
FIG. 4 shows a signal processing system for enhancing fine time structure perception of a cochlear prosthesis system, in accordance with an embodiment of the invention.

FIG. 4 shows a signal processing system 400 for enhancing fine time structure perception of a cochlear prosthesis system, in accordance with an embodiment of the invention. Illustratively, a cochlear implant prosthesis system is described, however various embodiments of the invention may include other types of hearing prosthesis known in the art, such as an auditory brain stimulator or middle ear prosthesis.

The system 400 includes one or more band-pass filters (BPFs) 402 which decompose an incoming speech signal or other audio input into multiple spectral bands. Each of the spectral bands undergoes further processing, ultimately producing pulses for an associated stimulation electrode implanted, without limitation, in the cochlea, or in the modiolus, or on or within an auditory structure in the brain. The processing elements associated with each electrode are typically referred to as a channel, a signal channel, or a stimulation channel. Processing elements of the system 400 may be external and/or internal (i.e., implanted) elements of the prosthesis system.

As described above with reference to FIG. 2, a zero crossing detector 404 may detect negative to positive crossings of their associated spectral band. A CSSS 406 may then be inserted at the start of the negative to positive zero crossings of their respective band pass filter output to create a sequence signal 408. Of course, other methodologies may be used with regard to the implementation of CSSS. For example, the output of each band pass filter may be rectified to create a half-wave rectified signal. Each half-wave may then be replaced with the channels associated CSSS to create the sequence signal 408.

An envelope detector 410 extracts the envelope of the spectral band signal, for example, by full-wave rectification and low pass filtering. The envelope, as described above, includes unresolved harmonics and is modulated with the difference tones of the harmonics, mainly the fundamental frequency F0.

In illustrative embodiments of the invention, the envelope of the band pass signal is filtered to reduce modulations resulting from unresolved harmonics, creating a filtered envelope signal 414. The reduction of amplitude modulations may be done in various ways.

For example, the band pass signal may be processed by a low pass filter 412, which may be adjustable. The low pass filter 412 may, without limitation, have a cut-off frequency $f_c$ that is lower than fundamental frequency F0 of the envelope. If the coding strategy is mainly designed to transmit human speech, then the cut-off frequencies of the low-pass filter may be selected in such a way, that substantially only envelope fluctuations in the range of human speech are transmitted. For example, and without limitation, the low pass filter may have a cut-off frequency $f_c$ of 10 Hz$\leq f_c \leq$90 Hz. Most of the temporal fluctuations of speech are slower than 50 Hz (see Steeneken, "A Physical Method for Measuring Speech Transmission Quality," J Acoust Soc Am 67:318-326, 1980, which is hereby incorporated herein by reference). Experiments showed that speech intelligibility is not significant different when reducing envelope fluctuations to 16 Hz (see: Shannon, "Speech Recognition with Primarily Temporal Cues," Science 270:303-304, 1995; and Drullman, "Effect of Reducing Slow Temporal Modulations on Speech Perception," J Acoust Soc Am 95: 2670-2680 1994, both of which are hereby incorporated herein by reference).

In other embodiments, the filtering of the envelope to reduce amplitude modulations may be done, without limitation, by isolating the dominating harmonics of the frequency spectral band, so that there is only one harmonic left per frequency spectral band. The selection of this dominating harmonic may be done, for example, with psychoacoustic masking models and an additional high resolution filter bank (time signal or FFT) with such a fine resolution, that the analysis frequency bands used for the selection includes only resolved harmonics.

The sampling sequence 408 is weighted with the filtered envelope signal 414 via a modulator 416. The output 418 of the modulator 416 may undergo further processing 420, such as, but not limited to compression/non-linear mapping and/or patient specific scaling, whereupon a stream of stimulation pulses are provided to the channel's associated electrode.

Figure 5:
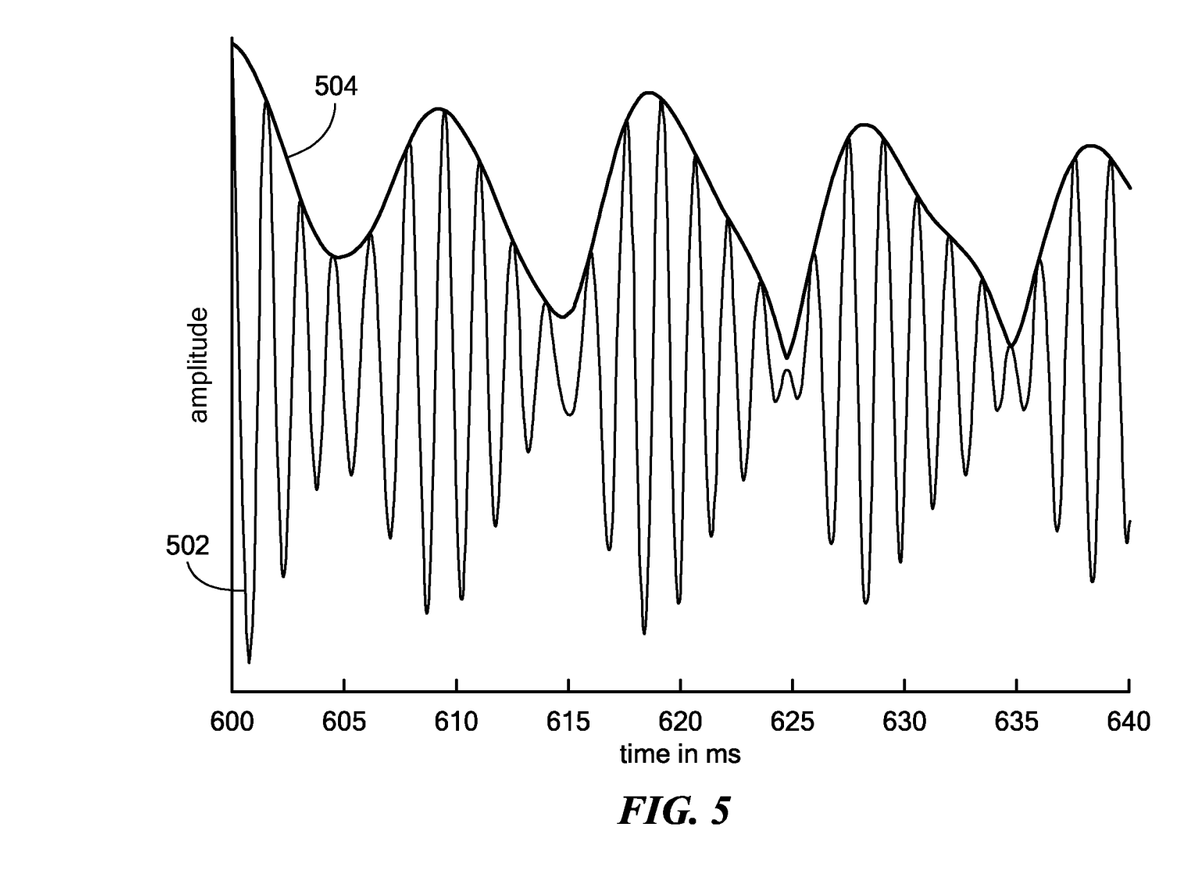
FIG. 5 shows the output of a band pass filter with a lower cutoff frequency 325 Hz and an upper cutoff frequency 490 Hz, with an audio signal input representing the recording of the syllable "aba", spoken by a male talker with an F0 of approximately 100 Hz.
Figure 6:
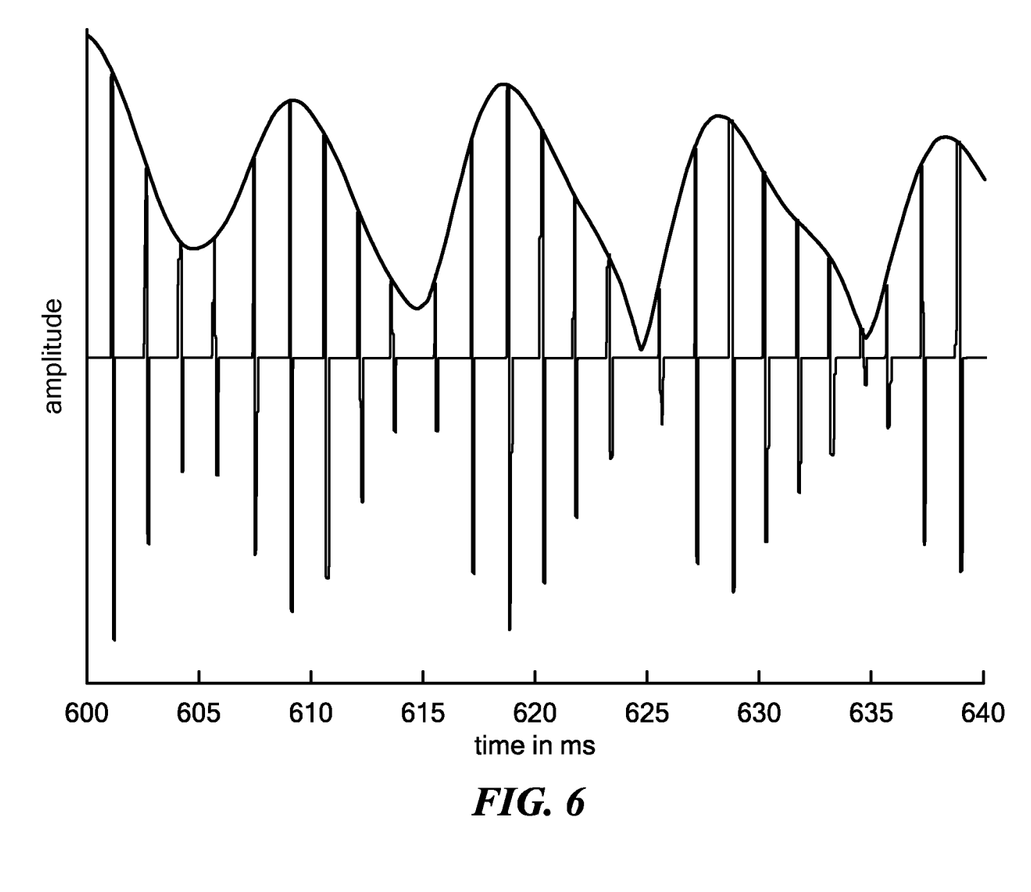
FIG. 6 shows biphasic pulses, applied at zero crossings of the band pass signal of FIG. 5, weighted with the signal's envelope (without filtering to reduce amplitude modulations)

FIG. 5 shows the output 502 of a band pass filter with a lower cutoff frequency 325 Hz and an upper cutoff frequency 490 Hz, with an audio signal input representing the recording of the syllable "aba", spoken by a male talker with an F0 of approximately 100 Hz. The signal envelope 504 is clearly modulated with F0. FIG. 6 shows biphasic pulses, applied at zero crossings of the band pass signal, weighted with the signal's envelope 504 (without filtering to reduce amplitude modulations). Similar to the signal envelope 504, the weighted sequence of biphasic pulses is also clearly modulated with F0. As described above, such modulation may prevent a cochlear implant user from perceiving fine time structure cues.

Figure 7:
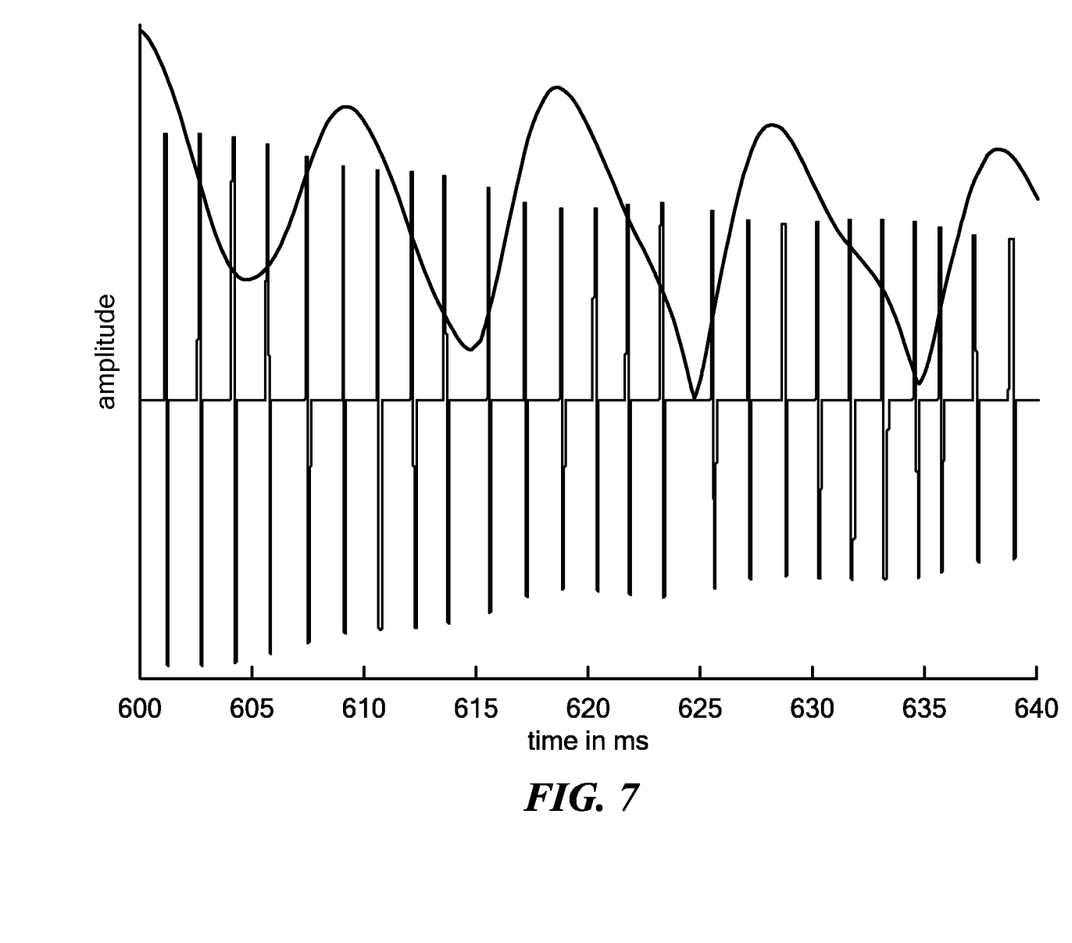
FIG. 7 shows same biphasic pulses weighted with a low pass filtered signal envelope, in accordance with an embodiment of the invention.

FIG. 7 shows the same biphasic pulses weighted with the low pass filtered signal envelope, in accordance with above described embodiments of the invention. The cut-off frequency of the low-pass filter is set to 50 Hz in this example. The reduction of amplitude modulations in FIG. 7 as compared to FIG. 6 advantageously leads to better perception of the fine time information included in the carrier pulses.

Embodiments of the invention may be implemented in whole or in part in any conventional computer programming language. For example, preferred embodiments may be implemented in a procedural programming language (e.g., "C") or an object oriented programming language (e.g., "C++" or Python). Alternative embodiments of the invention may be implemented as pre-programmed hardware elements, other related components, or as a combination of hardware and software components.

Embodiments can be implemented in whole or in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve at least some of the advantages of the invention without departing from the true scope of the invention. For example, the approaches described herein could be applied for auditory prostheses other than cochlear implants such as an auditory brainstem implant—with the electrical stimuli presented by electrodes within or adjacent to the cochlear nucleus—or the auditory midbrain implant—with the electrical stimuli presented by electrodes on or within the inferior colliculus.

The embodiments of the invention described above are intended to be merely exemplary; numerous variations and modifications will be apparent to those skilled in the art. All such variations and modifications are intended to be within the scope of the present invention. These and other obvious modifications are intended to be covered by the claims that follow.

What is claimed is:

1. A method of signal processing for a hearing implant, the hearing implant including at least one electrode, each electrode associated with a channel specific sampling sequence, the method comprising:
   processing an acoustic audio signal to generate for each electrode a band pass signal representing an associated band of audio frequency;
   determining for each electrode a sequence signal as a function of the electrode's associated band pass signal and channel specific sampling sequence;
   determining an envelope of each band pass signal;
   filtering the envelope of each band pass signal to reduce modulations resulting from unresolved harmonics, creating for each electrode an associated filtered envelope signal; and
   weighting each electrode's sequence signal based, at least in part, on the electrode's associated filtered envelope signal.

2. The method according to claim 1, wherein filtering the envelope of each band pass signal includes low pass filtering.

3. The method according to claim 2, wherein low pass filtering includes using a cut-off frequency that is lower than the fundamental frequency of the acoustic audio signal.

4. The method according to claim 2, wherein low pass filtering includes using a cut-off frequency $f_c$ of 15 Hz$\leq f_c \leq$90 Hz.

5. The method according to claim 1, wherein filtering the envelope of each band pass signal includes removing the fundamental frequency associated with the band pass signal.

6. The method according to claim 1, wherein filtering the envelope of each band pass filter results in a filtered envelope signal with only one harmonic.

7. The method according to claim 1, wherein the filtering includes using at least one of a psychoacoustic masking model and a high resolution filter bank.

8. The method according to claim 1, wherein determining for each electrode a sequence signal as a function of the electrode's associated band pass signal and channel specific sampling sequence includes:
   a. rectifying the electrode's associated band pass signal to create a half-wave rectified signal; and
   b. replacing each half-wave with the associated electrode's channel specific sampling sequence.

9. The method according to claim 1, wherein determining for each electrode a sequence signal as a function of the electrode's associated band pass signal and channel specific sampling sequence includes:
   a. determining negative to positive zero crossings of the electrode's associated band pass signal; and
   b. inserting at the negative to positive zero crossings the electrode's associated channel specific sampling sequence.

10. The method according to claim 1, further comprising stimulating the at least one electrode based, at least in part, on their associated weighted sequence signal.

11. The method according to claim 10, wherein the hearing implant is a cochlear implant, and wherein stimulating includes stimulating the acoustic nerve.

12. A hearing system comprising:
   at least one electrode, each electrode associated with a channel specific sampling sequence;
   a signal processor configured to:
      process an acoustic audio signal to generate for each electrode a band pass signal representing an associated band of audio frequency;
      determining for each electrode a sequence signal as a function of the electrode's associated band pass signal and channel specific sampling sequence;
      determine an envelope of each band pass signal;
      filter the envelope of each band pass signal to reduce modulations resulting from unresolved harmonics, creating for each electrode an associated filtered envelope signal; and
      weight each electrode's sequence signal based, at least in part, on the electrode's associated filtered envelope signal.

13. The hearing system according to claim 12, wherein the signal processor includes a low pass filter for filtering the envelope of each band pass signal.

14. The hearing system according to claim 13, wherein the low pass filter includes a cut-off frequency that is lower than the fundamental frequency of the acoustic audio signal.

15. The hearing system according to claim 13, wherein the low pass filter includes a cut-off frequency $f_c$ of 15 Hz $\leq f_c \leq$ 90 Hz.

16. The hearing system according to claim 12, wherein the signal processor removes the fundamental frequency associated with the band pass signal.

17. The hearing system according to claim 12, wherein the signal processor includes at least one of a psychoacoustic masking model and a high pass resolution filter bank for filtering the envelope of each band pass signal to create a filtered envelope signal with only one harmonic.

18. The hearing system according to claim 12, wherein the signal processor includes a rectifier for rectifying the electrode's associated band pass signal to create a half-wave rectified signal, and wherein the signal processor is configured to replace each half-wave with the associated electrode's channel specific sampling sequence in determining the sequence signal.

19. The hearing system according to claim 12, wherein the signal processor includes a zero crossing detector for determining negative to positive zero crossings of the electrode's associated band pass signal; and wherein the signal processor is configured to inserting at the negative to positive zero crossings the electrode's associated channel specific sampling sequence in determining the sequence signal.

20. The hearing system according to claim 12, further comprising a stimulator for stimulating the at least one electrodes based, at least in part, on their associated weighted sequence signal.

21. The hearing system according to claim 12, wherein the hearing system is a cochlear prosthesis system, and wherein the stimulator is capable of being implanted so as to stimulate the acoustic nerve.

22. A computer program product for processing signals associated with a hearing implant, the hearing implant including at least one electrode, each electrode associated with a channel specific sampling sequence, the computer program product comprising a non-transitory computer readable medium having computer readable program code thereon, the computer readable program code comprising:
   program code for generating a band pass signal for each electrode representing an associated band of audio frequency based at least in part, on an acoustic audio signal;
   program code for determining for each electrode a sequence signal as a function of the electrode's associated band pass signal and channel specific sampling sequence;
   program code for determining an envelope of each band pass signal;
   program code for filtering the envelope of each band pass signal to reduce modulations resulting from unresolved harmonics, creating for each electrode an associated filtered envelope signal; and
   program code for weighting each electrode's sequence signal based, at least in part, on the electrode's associated filtered envelope signal.

* * * * *